US011511098B2

United States Patent
Agrawal et al.

(10) Patent No.: US 11,511,098 B2
(45) Date of Patent: Nov. 29, 2022

(54) LOW PRESSURE SEAL DESIGN FOR A HEMOSTASIS VALVE

(71) Applicant: BOSTON SCIENTIFIC LIMITED, Hamilton (BM)

(72) Inventors: Sumit Agrawal, Gurgaon (IN); Biten Kishore Kathrani, Mumbai (IN)

(73) Assignee: BOSTON SCIENTIFIC LIMITED, Hamilton (BM)

( * ) Notice: Subject to any disclaimer, the term of this patent is extended or adjusted under 35 U.S.C. 154(b) by 745 days.

(21) Appl. No.: 15/806,302

(22) Filed: Nov. 7, 2017

(65) Prior Publication Data

US 2018/0126143 A1 May 10, 2018

Related U.S. Application Data

(60) Provisional application No. 62/419,699, filed on Nov. 9, 2016.

(51) Int. Cl.
*A61M 39/06* (2006.01)

(52) U.S. Cl.
CPC ........ *A61M 39/0606* (2013.01); *A61M 39/06* (2013.01); *A61M 2039/062* (2013.01);
(Continued)

(58) Field of Classification Search
CPC .............. A61M 39/06; A61M 39/0606; A61M 2039/062; A61M 2039/064;
(Continued)

(56) References Cited

U.S. PATENT DOCUMENTS 4,673,393 A * 6/1987 Suzuki .............. A61M 39/0606
 138/89
5,154,701 A * 10/1992 Cheer ............... A61M 39/0606
 137/849

(Continued)

FOREIGN PATENT DOCUMENTS

DE 19914148 A1 10/1999
EP 0198962 A1 10/1986
(Continued)

OTHER PUBLICATIONS

"generally". Merriam-Webster Dictionary. https://www.merriam-webster.com/dictionary/generally Accessed Oct. 2020. (Year: 2020).*
(Continued)

*Primary Examiner* — Bhisma Mehta
*Assistant Examiner* — Nidah Hussain
(74) *Attorney, Agent, or Firm* — Seager, Tufte & Wickhem LLP

(57) ABSTRACT

A hemostasis valve assembly for use in a medical device. The hemostasis valve assembly may include a main body portion defining an internal cavity, a seal cartridge disposed within the internal cavity, and a low pressure valve assembly positioned within the internal cavity adjacent to the seal cartridge. The low pressure valve assembly may include a first valve member having a first valve body and a second valve member having second valve body. A portion of a distal side of the first valve member may abut at least a portion of a proximal side of the second valve member.

19 Claims, 12 Drawing Sheets

(52) U.S. Cl.
CPC ............. *A61M 2039/064* (2013.01); *A61M 2039/0686* (2013.01); *A61M 2205/0216* (2013.01)

(58) Field of Classification Search
CPC .. A61M 2039/0686; A61M 2205/0216; A61M 2039/0646; A61M 16/20; A61M 39/20
USPC ....................................................... 604/167
See application file for complete search history.

(56) References Cited

U.S. PATENT DOCUMENTS

| | | | |
|---|---|---|---|
| 5,195,980 A * | 3/1993 | Catlin | A61M 39/0693 604/167.04 |
| 5,591,137 A | 1/1997 | Stevens | |
| 5,603,702 A * | 2/1997 | Smith | A61M 39/06 604/167.03 |
| 5,643,227 A | 7/1997 | Stevens | |
| 5,693,025 A | 12/1997 | Stevens | |
| 6,149,632 A * | 11/2000 | Landuyt | A61M 5/00 604/201 |
| 6,610,031 B1 * | 8/2003 | Chin | A61M 39/0606 604/167.04 |
| 9,974,938 B2 | 5/2018 | Pepin et al. | |
| 10,188,845 B2 | 1/2019 | Fischer et al. | |
| 2002/0010425 A1 * | 1/2002 | Guo | A61M 39/06 604/167.04 |
| 2004/0210194 A1 * | 10/2004 | Bonnette | A61B 17/32037 604/167.06 |
| 2006/0145116 A1 | 7/2006 | Rickerd et al. | |
| 2008/0128646 A1 * | 6/2008 | Clawson | F16L 55/1155 215/329 |
| 2009/0012476 A1 | 1/2009 | Catlin | |
| 2010/0280456 A1 * | 11/2010 | Nijland | A61M 39/06 604/167.03 |
| 2015/0157843 A1 | 6/2015 | Pepin et al. | |

FOREIGN PATENT DOCUMENTS

| | | |
|---|---|---|
| JP | S6115679 A | 7/1986 |
| JP | H0947511 A | 2/1997 |
| JP | H11319115 A | 11/1999 |

OTHER PUBLICATIONS

International Search Report and Written Opinion for Application No. PCT/US2017/060475, 26 pages, dated Feb. 28, 2018.

* cited by examiner

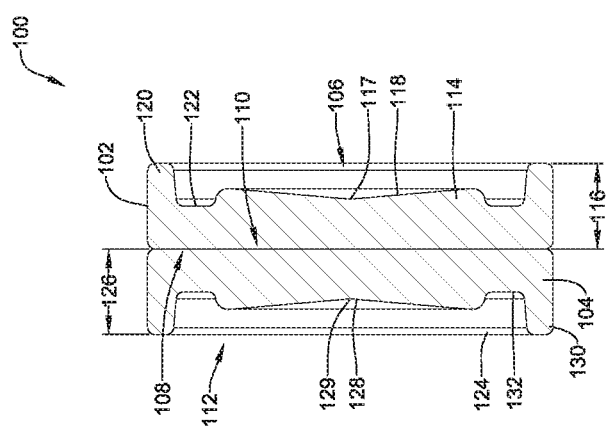

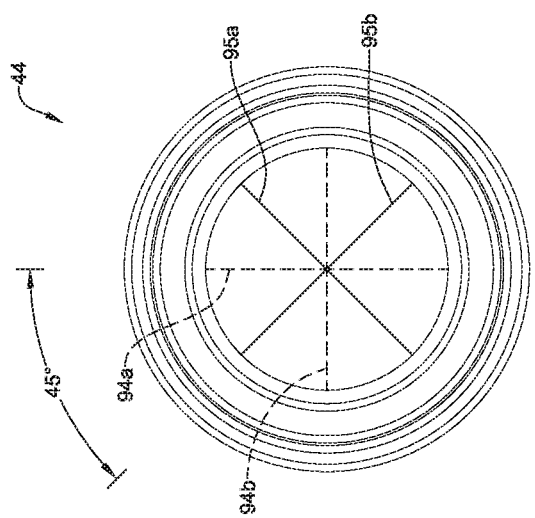

LOW PRESSURE SEAL DESIGN FOR A HEMOSTASIS VALVE

CROSS REFERENCE TO RELATED APPLICATIONS

This application claims the benefit of U.S. Provisional Patent Application Ser. No. 62/419,699 filed on Nov. 9, 2016, the disclosure of which is incorporated herein by reference.

TECHNICAL FIELD

The disclosure is directed to a hemostasis valve. More particularly, the disclosure is directed to a hemostasis valve including a low pressure seal.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing methods, and use alternatives for medical devices.

In a first example, a hemostasis valve assembly for use in a medical device may comprise, a main body portion defining an internal cavity, a seal cartridge disposed within the internal cavity, and a low pressure valve assembly positioned within the internal cavity adjacent to the seal cartridge. The low pressure valve assembly may comprise a first valve member including a first valve body having a proximal side, a distal side, and a thickness therebetween and a second valve member including a second valve body having a proximal side, a distal side, and a thickness therebetween. At least a portion of the distal side of the first valve member may abut at least a portion of the proximal side of the second valve member.

Alternatively or additionally to any of the examples above, in another example, the proximal side of the first valve member may have an angled central region and the distal side of the first valve member may be generally planar.

Alternatively or additionally to any of the examples above, in another example, the distal side of the second valve member may have an angled central region and the proximal side of the second valve member may be generally planar.

Alternatively or additionally to any of the examples above, in another example, the proximal side of the second valve member may include a tapered central region having a surface sloped towards a center of the second valve body and the distal side of the second valve member may include a distally extending curved central region.

Alternatively or additionally to any of the examples above, in another example, the low pressure valve assembly may comprise an elastomeric silicone.

Alternatively or additionally to any of the examples above, in another example, the low pressure valve assembly may comprise a liquid silicone rubber (LSR).

Alternatively or additionally to any of the examples above, in another example, the low pressure valve assembly may comprise an enhanced tear resistant (ETR) silicone elastomer.

Alternatively or additionally to any of the examples above, in another example, the first valve member may comprise a first elastomeric material and the second valve member may comprise a second elastomeric material different from the first elastomeric material.

Alternatively or additionally to any of the examples above, in another example, the hemostasis valve assembly may further comprise one or more slits formed in the first valve body and extending at least partially through the thickness of the first valve body and one or more slits formed in the second valve body and extending at least partially through the thickness of the second valve body.

Alternatively or additionally to any of the examples above, in another example, the one or more slits in the first valve body and the one or more slits in the second valve body may be formed in a cross slit thru (CST) configuration.

Alternatively or additionally to any of the examples above, in another example, the one or more slits in the first valve body and the one or more slits in the second valve body may be formed in a star slit thru (SST) configuration.

Alternatively or additionally to any of the examples above, in another example, at least one of the one or more slits in the first valve body or the one or more slits in the second valve body may be formed in a star slit thru (SST) configuration and the other of the one or more slits in the first valve body or the one or more slits in the second valve body may be formed in a cross slit thru (CST) configuration.

Alternatively or additionally to any of the examples above, in another example, the one or more slits in the first valve body may be radially offset from the one or more slits in the second valve body.

Alternatively or additionally to any of the examples above, in another example, at least one of the one or more slits in the first valve body or the one or more slits in the second valve body may be formed in a cross slit partial (CSP) configuration.

Alternatively or additionally to any of the examples above, in another example, the hemostasis valve assembly may further comprise a high pressure seal disposed in the internal cavity, the high pressure seal positioned distal to the low pressure seal assembly.

In another example, a hemostasis valve assembly for use in a medical device may comprise a main body portion defining an internal cavity, a seal cartridge disposed within the internal cavity, and a low pressure valve assembly positioned within the internal cavity adjacent to the seal cartridge. The low pressure valve assembly may comprise a first valve member including a first valve body having a proximal side, a distal side, and a thickness therebetween and a second valve member including a second valve body having a proximal side, a distal side, and a thickness therebetween. At least a portion of the distal side of the first valve member may abut at least a portion of the proximal side of the second valve member.

Alternatively or additionally to any of the examples above, in another example, the proximal side of the first valve member may have an angled central region and the distal side of the first valve member may be generally planar.

Alternatively or additionally to any of the examples above, in another example, the distal side of the second valve member may have an angled central region and the proximal side of the second valve member may be generally planar.

Alternatively or additionally to any of the examples above, in another example, the proximal side of the second valve member may include a tapered central region having a surface sloped towards a center of the second valve body and the distal side of the second valve member may include a distally extending curved central region.

Alternatively or additionally to any of the examples above, in another example, the low pressure valve assembly may comprise an elastomeric silicone.

Alternatively or additionally to any of the examples above, in another example, the first valve member may comprise a first elastomeric material and the second valve member may comprise a second elastomeric material different from the first elastomeric material.

Alternatively or additionally to any of the examples above, in another example, the hemostasis valve assembly may further comprise one or more slits formed in the first valve body and extending at least partially through the thickness of the first valve body and one or more slits formed in the second valve body and extending at least partially through the thickness of the second valve body.

Alternatively or additionally to any of the examples above, in another example, the one or more slits in the first valve body and the one or more slits in the second valve body may be formed in a cross slit thru (CST) configuration, a star slit thru (SST) configuration, a cross slit partial (CSP) configuration, or combinations thereof.

Alternatively or additionally to any of the examples above, in another example, the one or more slits in the first valve body may be radially offset from the one or more slits in the second valve body.

In another example, a hemostasis valve assembly for use in a medical device may comprise a main body portion defining an internal cavity, a seal cartridge disposed within the internal cavity, and a low pressure valve assembly positioned within the internal cavity adjacent to the seal cartridge. The low pressure valve assembly may comprise a first valve member including a first valve body having a proximal side, a distal side, and a thickness therebetween. The proximal side of the first valve member may have an angled central region and the distal side of the first valve member may be generally planar. The low pressure valve assembly may further comprise a second valve member including a second valve body having a proximal side, a distal side, and a thickness therebetween. The distal side of the second valve member may have an angled central region and the proximal side of the second valve member may be generally planar. At least a portion of the distal side of the first valve member may abut at least a portion of the proximal side of the second valve member.

Alternatively or additionally to any of the examples above, in another example, the low pressure valve assembly may comprise an elastomeric silicone.

Alternatively or additionally to any of the examples above, in another example, the first valve member may comprise a first elastomeric material and the second valve member may comprise a second elastomeric material different from the first elastomeric material.

Alternatively or additionally to any of the examples above, in another example, the hemostasis valve assembly may further comprise one or more slits formed in the first valve body and extending at least partially through the thickness of the first valve body and one or more slits formed in the second valve body and extending at least partially through the thickness of the second valve body.

Alternatively or additionally to any of the examples above, in another example, the one or more slits in the first valve body and the one or more slits in the second valve body may be formed in a cross slit thru (CST) configuration, a star slit thru (SST) configuration, a cross slit partial (CSP) configuration, or combinations thereof.

Alternatively or additionally to any of the examples above, in another example, the one or more slits in the first valve body may be radially offset from the one or more slits in the second valve body.

In another example, a hemostasis valve assembly for use in a medical device may comprise a main body portion defining an internal cavity, a seal cartridge disposed within the internal cavity, and a low pressure valve assembly positioned within the internal cavity adjacent to the seal cartridge. The low pressure valve assembly may comprise a first valve member including a first valve body having a proximal side, a distal side, and a thickness therebetween. The proximal side of the first valve member may have an angled central region and the distal side of the first valve member may be generally planar. The low pressure valve assembly may further comprise a second valve member including a second valve body having a proximal side, a distal side, and a thickness therebetween. The proximal side of the second valve member may include a tapered central region having a surface sloped towards a center of the second valve body and the distal side of the second valve member may include a distally extending curved central region. At least a portion of the distal side of the first valve member may abut at least a portion of the proximal side of the second valve member.

Alternatively or additionally to any of the examples above, in another example, the low pressure valve assembly may comprise one or more elastomeric materials.

Alternatively or additionally to any of the examples above, in another example, the hemostasis valve assembly may further comprise one or more slits formed in the first valve body and extending at least partially through the thickness of the first valve body and one or more slits formed in the second valve body and extending at least partially through the thickness of the second valve body.

Alternatively or additionally to any of the examples above, in another example, the one or more slits in the first valve body and the one or more slits in the second valve body may be formed in a cross slit thru (CST) configuration, a star slit thru (SST) configuration, a cross slit partial (CSP) configuration, or combinations thereof.

Alternatively or additionally to any of the examples above, in another example, the one or more slits in the first valve body may be radially offset from the one or more slits in the second valve body.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which:

FIG. 6 is a cross-sectional view of the low pressure seal assembly of FIG. 5, taken at line 6-6 in FIG. 5;

FIGS. 8A-8C are proximal end views of an illustrative low pressure seal assembly illustrating some possible combinations of a slit configuration.

Figure 1:
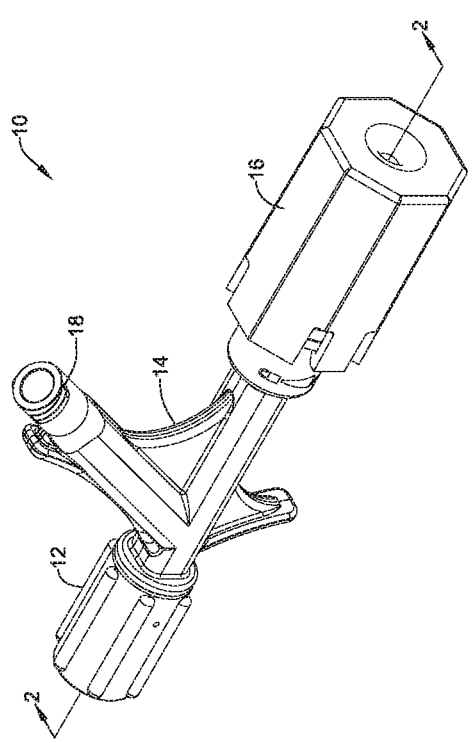
FIG. 1 is a perspective view of an illustrative hemostasis valve assembly.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

FIG. 1 is a perspective view of an illustrative hemostasis valve assembly 10. The hemostasis valve assembly 10 may be used to couple a diagnostic or interventional device (not explicitly shown) to a high pressure fluid delivery system (e.g., a high pressure contrast injection) (not explicitly shown). However, the hemostasis valve assembly 10 may be used in other procedures. The hemostasis valve assembly 10 may include an adaptor 12 configured to removably couple the hemostasis valve assembly 10 to the diagnostic or interventional device. The hemostasis valve assembly 10 may further include a main body portion 14 and a plunger 16. The main body portion 14 may include a side port 18 for connection to a flush or injection tube subassembly (not explicitly shown).

Figure 2:
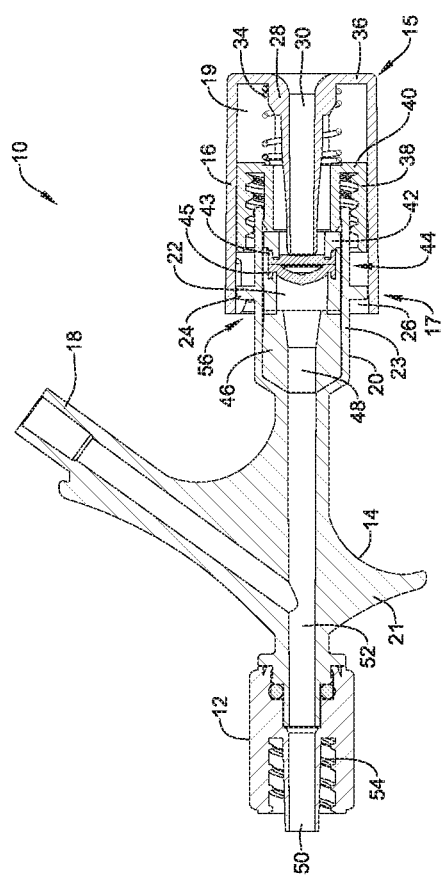
FIG. 2 is a cross-sectional view of the illustrative hemostasis valve assembly of FIG. 1, taken at line 2-2.

FIG. 2 is cross-sectional view of the illustrative hemostasis valve assembly 10 of FIG. 1 taken at line 2-2 in FIG. 1. The adaptor 12 may include a lumen 50 extending therethrough to fluidly couple the diagnostic or interventional device with a fluid source and/or to allow for the passage of other devices. The adaptor 12 may include a region of internal threads 54 configured to engage and releasably couple with corresponding threads on the diagnostic or interventional device. However, other coupling mechanism may be used including, but not limited to friction fits, snap fits, etc.

The main body portion 14 may include a proximal portion 20 and a distal portion 21. The distal portion 21 may be coupled to the adaptor 12. The proximal portion 20 may be slidably coupled to the plunger 16. The plunger 16 may be a generally hollow cylindrical structure having a proximal end 15, a distal end 17, and an internal cavity 19. The proximal end 15 may have an annular proximal end wall 36 while the distal end defines an opening 56 for slidably receiving the main body portion 14. A mechanical stop mechanism 26, such as protrusions, may be positioned adjacent to a distal end 17 of the plunger 16. The mechanical stop mechanism 26 are configured to engage a mechanical stop mechanism 24 extending from a side wall 23 of the proximal portion 20 of the main body portion 14 to limit proximal movement of the plunger 16 relative to the main body portion 14. A capillary 28 may extend distally from the annular proximal end wall 36 of the plunger 16 and into the internal cavity 19. The capillary 28 includes a lumen 30 configured to fluidly couple a fluid device (not explicitly shown) with a lumen 52 of the main body portion 14, the lumen 50 of the adaptor 12, and ultimately a diagnostic or interventional device coupled to the adaptor 12. The plunger 16 may include a spring 34 configured to bias the plunger 16 in a proximal direction.

A lock nut 38 may be disposed within the cavity 19 of the plunger 16. The lock nut 38 may be configured to move along the side wall 23 and to threadably engage a mating feature on the side wall 23 (e.g., on the internal or external surface, as desired) of the proximal portion 20 of the adaptor 12. As will be described in more detail herein, during use, the lock nut 38 may be used to lock the plunger 16 to a distally advanced configuration. A seal cartridge 42 may be positioned distal to the lock nut 38. The seal cartridge 42 may be configured to hold a low pressure seal (or valve) assembly 44 in a fixed position within an internal cavity 22 of the proximal portion 20 of the main body portion 14. For example, as described in more detail herein, a portion of the low pressure seal assembly 44 may be received in one or more grooves or recesses 43, 45 in the seal cartridge 42. A high pressure seal 46 may be disposed distal to the low pressure seal assembly 44. The high pressure seal 46 may have a lumen 48 extending therethrough. The lumen 48 of the high pressure seal 46 may have a diameter or diameter profile (e.g., variable diameter along a length) that is substantially the same as, or slightly smaller than an outer diameter or diameter profile of the capillary 28. As will be described in more detail herein, this may create a frictional fit between the lumen 48 and the capillary 28 when the plunger 16 is in a distally advanced configuration.

During use, for example, when a high pressure contrast injection is desired, a clinician may exert a distal pushing force on the plunger 16 sufficient to overcome the proximal biasing force of the spring 34. The spring 34 may compress allowing the plunger 16 to advance distally over the proximal portion 20 of the main body portion 14 until the annular proximal end wall 36 contacts a proximal end surface 40 of the lock nut 38. The user may then apply a radially applied gripping force to rotate the plunger 16 and the lock nut 38 to further distally advance the plunger 16 and the lock nut 38. When the plunger 16 and the lock nut 38 are in the desired longitudinal position, the threaded engagement of the lock nut 38 and the proximal portion 20 of the main body portion 14 may be sufficient to lock the main body portion 14 in a distally advanced configuration. As will be described in more detail herein, the low pressure seal assembly 44 may include slits or other mechanisms to allow the capillary 28 to advance distally within the cavity 22 and lumen 48 of the high pressure seal 46. In the distally advanced configuration, the outer surface of the capillary 28 may frictionally engage the surface of the lumen 48 in the high pressure seal 46. This may create a seal which prevents the high pressure fluid from leaking from the hemostasis valve assembly 10.

It is contemplated that the plunger 16 is in the proximally retracted configuration (shown in FIG. 2) during some interventional and diagnostic procedures (also referred to as the normal use of the hemostasis valve assembly 10) and in the distally advanced configuration for the delivery of a high pressure interventional or diagnostic fluid. In the proximally retracted configuration, the capillary 28 is not engaged with the lumen 48 of the high pressure seal 46 and hence does not prevent fluid from leaking from the hemostasis valve assembly 10. The low pressure seal assembly 44 may be configured to prevent blood loss (or other fluid loss) during normal use of the hemostasis valve assembly 10. In some cases, the low pressure seal assembly 44 may be provided as a single molded part. Increasing the thickness of a single molded low pressure seal assembly 44 may improve the performance of the low pressure seal assembly 44, but may negatively affect the insertion force of the plunger 16 (e.g., more force may be needed to distally advance the plunger 16). The low pressure seal assembly 44 may be provided a two-part assembly which may improve performance of the seal without negatively affecting the insertion force of the plunger 16.

Figure 3:
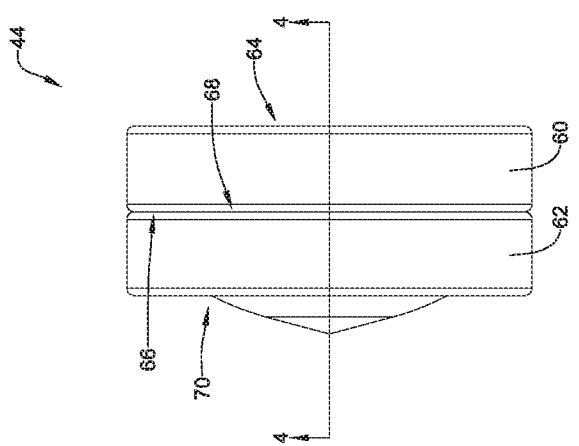
FIG. 3 is side view of an illustrative low pressure seal assembly.

FIG. 3 is a side view of an illustrative low pressure seal assembly 44 that may be used with the hemostasis valve assembly 10. The low pressure seal assembly 44 may include a first gasket or valve member 60 having a proximal side 64 and a distal side 66 and a second gasket or valve member 62 having a proximal side 68 and a distal side 70. At least a portion of the distal side 66 of the first valve member 60 may abut or contact at least a portion of the proximal side 68 of the second valve member 62. As will be described in more detail herein, each of the valve member 60 and the valve member 62 may include one or more slits arranged to allow the low pressure seal assembly 44 to flex in a central region thereof.

Figure 4:
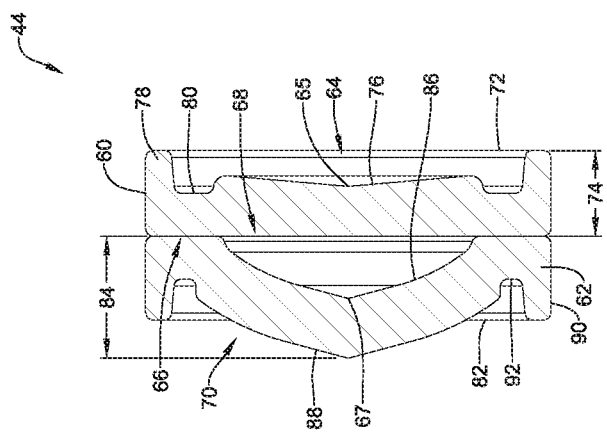
FIG. 4 is a cross-sectional view of the low pressure seal assembly of FIG. 3, taken at line 4-4 in FIG. 3.

FIG. 4 is a cross-sectional view of the illustrative low pressure seal assembly 44 of FIG. 3, taken at line 4-4 in FIG. 3. The first valve member 60 may have a generally cylindrical, puck-like first valve body 72 having thickness 74 extending between the proximal side 64 and the distal side 66. The first valve member 60 may be formed from an elastomeric silicone or other compliant material which allows the first valve member 60 to resume its original shape after temporary deformation (e.g., an applied stress or force less than the yield point or fracture point). Some illustrative materials may include, but are not limited to, a liquid silicone rubber (LSR) elastomer or enhanced tear resistant (ETR) silicone elastomers.

The proximal side 64 of the first valve member 60 may include a slightly angled or tapered central region 76 with the surface sloped towards a diametrical center 65 of the valve member 60. The distal side 66 of the first valve member 60 may be generally planar. The first valve member 60 may include a flanged outer perimeter 78. The flanged outer perimeter 78 may have an increased thickness (e.g., in the proximal to distal direction) relative to an annular groove 80 formed in the proximal side 64 of the first valve member 60. The groove 80 in combination with the flanged outer perimeter 78 may form an interlocking mechanism configured to engage the groove or recess 43 in the seal cartridge 42. In some embodiments, the thickness 74 of the valve body 72 may vary across the diameter thereof. For example, the thickness of the valve body 72 adjacent to the diametrical center 65 may be less than the thickness 74 at the flanged outer perimeter 78 but greater than the annular groove 80. This is just an example, it is contemplated that the thickness may vary in any manner desired.

The second valve member 62 may have a generally cylindrical, puck-like second valve body 82 having a thickness 84 extending between the proximal side 68 and the distal side 70. The second valve member 62 may be formed from an elastomeric silicone or other compliant material which allows the second valve member 62 to resume its original shape after temporary deformation (e.g., an applied stress or force less than the yield point or fracture point). Some illustrative materials may include, but are not limited to, a liquid silicone rubber (LSR) elastomer or enhanced tear resistant (ETR) silicone elastomers.

The proximal side 68 of the second valve member 62 may include a tapered or conical central region 86 with the surface sloped towards the diametrical center 67 of the second valve member 62. The tapered central region 86 decreases in diameter from the proximal side 68 towards the distal side 70 of the second valve member 62. The tapered central region 86 may guide the capillary 28, or other supplemental medical device, towards the diametrical center 67 of the second valve member 62. The tapered central region 86 may act as a self-centering mechanism which automatically guides capillary 28 (or other supplemental medical device) towards the center of the second valve member 62 during use. The self-centering mechanism may reduce the force required to push the capillary 28, or other supplemental medical device through the second valve member 62 and/or reduce the number of attempts necessary to pass a device through the second valve member 62.

The distal side 70 of the second valve member 62 may include a distally extending curved or convex central region 88. The curvature of the central region 88 may help close the second valve member 62 when blood, or other fluid, pushes against the distal side 70 of the second valve member 62. It is contemplated that increasing or decreasing the curvature of the central region 88 may alter the effectiveness of the closure of the second valve member 62.

The second valve member 62 may include a flanged outer perimeter 90. The flanged outer perimeter 90 may have an increased thickness (e.g., in the proximal to distal direction) relative to an annular groove 92 formed in the distal side 70 of the valve member 62. The groove 92 in combination with the flanged outer perimeter 90 may form an interlocking mechanism configured to engage the groove or recess 45 in the seal cartridge 42. The thickness of the second valve member 62 may vary across the diameter thereof. For example, a thickness adjacent to the annular groove 92 may be greater than a thickness adjacent to the diametrical center 67 of the second valve member 62. It is contemplated reducing the thickness of the second valve member 62 adjacent to the center 67 may reduce the force required to advance a device through the second valve member 62. In some cases, the thickness of the flanged outer perimeter 90 may be the same as, similar to, or different from the other thicknesses of the second valve member 62, as desired. Other variations in the thickness(es) of the second valve member 62 are also contemplated. It is contemplated that changes in thickness may occur in a step-wise, or abrupt, manner or in a gradual, or smooth, manner, as desired. In some cases, the thickness may be uniform across the diameter of the second valve member 62.

Figure 5:
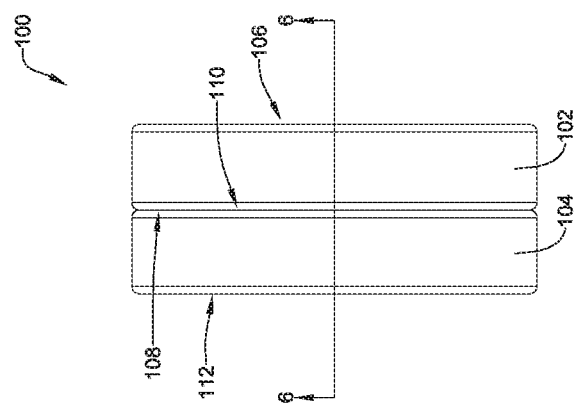
FIG. 5 is side view of another illustrative low pressure seal assembly.

FIG. 5 is a side view of another illustrative low pressure seal assembly 100 that may be used with the hemostasis valve assembly 10. The low pressure seal assembly 100 may be used in place of the low pressure seal assembly 44 in FIGS. 1-2. The low pressure seal assembly 100 may include a first gasket or valve member 102 having a proximal side 106 and a distal side 108 and a second gasket or valve member 104 having a proximal side 110 and a distal side 112. The first and second valve members 104 may be similar in form to the valve member 60 described herein. At least a portion of the distal side 108 of the first valve member 102 may abut or contact at least a portion of the proximal side 110 of the second valve member 104. As will be described in more detail herein, each of the first valve member 102 and the second valve member 104 may include one or more slits arranged to allow the low pressure seal assembly 100 to flex in a central region thereof.

FIG. 6 is a cross-sectional view of the illustrative low pressure seal assembly 100 of FIG. 5, taken at line 6-6 in FIG. 5. The first valve member 102 and the second valve member 104 may be identical components positioned in a mirror image arrangement. The first valve member 102 may have a generally cylindrical, puck-like first valve body 114 having a thickness 116 extending between the proximal side 106 and the distal side 108. The first valve member 102 may be formed from an elastomeric silicone or other compliant material which allows the first valve member 102 to resume its original shape after temporary deformation (e.g., an applied stress or force less than the yield point or fracture point). Some illustrative materials may include, but are not limited to, a liquid silicone rubber (LSR) elastomer or enhanced tear resistant (ETR) silicone elastomers.

The proximal side 106 of the first valve member 102 may include a slightly angled or tapered central region 118 with the surface sloped towards a diametrical center 117 of the first valve member 102. The distal side 108 of the first valve member 102 may be generally planar. The first valve member 102 may include a flanged outer perimeter 120. The flanged outer perimeter 120 may have an increased thickness (e.g., in the proximal to distal direction) relative to an annular groove 122 formed in the proximal side 106 of the first valve member 102. The groove 122 in combination with the adaptor 12 may form an interlocking mechanism configured to engage the groove or recess 43 in the seal cartridge 42.

The second valve member 104 may have a generally cylindrical, puck-like second valve body 124 having thickness 126 extending between the proximal side 110 and the distal side 112. The second valve member 104 may be formed from an elastomeric silicone or other compliant material which allows the second valve member 104 to resume its original shape after temporary deformation (e.g., an applied stress or force less than the yield point or fracture point). Some illustrative materials may include, but are not limited to, a liquid silicone rubber (LSR) elastomer or enhanced tear resistant (ETR) silicone elastomers.

The distal side 112 of the second valve member 104 may include a slightly angled or tapered central region 128 with the surface sloped towards a diametrical center of the second valve member 104. The proximal side 110 of the second valve member 104 may be generally planar. The second valve member 104 may include a flanged outer perimeter 130. The flanged outer perimeter 130 may have an increased thickness (e.g., in the proximal to distal direction) relative to an annular groove 132 formed in the distal side 112 of the second valve member 104. The groove 132 in combination with the flanged outer perimeter 130 may form an interlocking mechanism configured to engage the groove or recess 43 in the seal cartridge 42.

Figure 7A:
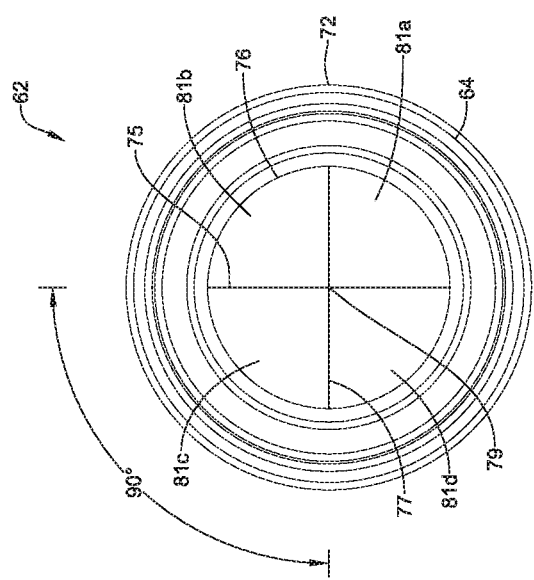
FIG. 7A is a proximal end view of an illustrative valve member having a first slit configuration.

FIG. 7A illustrates a proximal end view of the first valve member 60 having a first slit configuration. The use of the first valve member 60 is merely exemplary and it should be understood that any of one or more of the first valve member 60, the second valve member 62, the first valve member 102, and/or the second valve member 104 may include the slit configuration described with respect to FIG. 7A. For clarity, not all of the features of the first valve member 60 have been identified in FIG. 7A. The central region 76 of the first valve body 72 may include a vertical slit 75 and a horizontal slit 77 extending generally perpendicular to the vertical slit 75. The slits 75, 77 may both extend entirely through the thickness of the first valve member 60 from the proximal side 64 to the distal side 66 (e.g., in a cross slit thru (CST) configuration). The slits 75, 77 may intersect at an intersection point 79 in the diametrical center 65 of the first valve member 60 to define four flaps 81a, 81b, 81c, 81d (collectively, 81). The number and orientation of slits 75, 77 may be varied to vary a number of flaps 81, as desired. While the slits 75, 77 are described and shown as extending in a horizontal and vertical orientation, it is contemplated that the slits 75, 77 may be rotated such that the slits 75, 77 are offset from the horizontal and vertical axes. It is further contemplated that the slits 75, 77 may not necessarily intersect at a 90° angle. The intersection angle may be varied to create flaps 81 of varying size (e.g., two smaller and two larger). The flaps 81 may bend or flex in the distal direction as the capillary 28 (or other supplemental medical device) is passed through the first valve member 60. Once distal movement of the capillary 28 (or other supplemental medical device) ceased (and the distal biasing force is removed from the first valve member 60), the flow of blood from the distal side 66 may bias the flaps 81 proximally causing the flaps 81 to seal around an outer surface of the capillary 28 (or other supplemental medical device) as well as bringing the flaps 81 into intimate contact adjacent to the slits 75, 77.

Figure 7B:
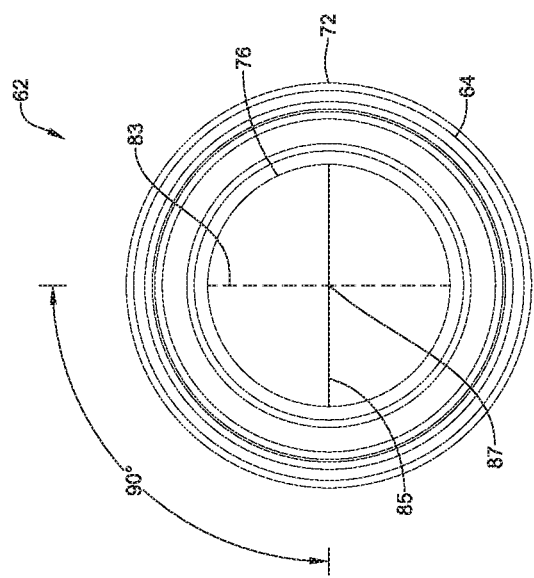
FIG. 7B is a proximal end view of an illustrative valve member having a second slit configuration.

FIG. 7B illustrates a proximal end view of the first valve member 60 having a second slit configuration. The use of the first valve member 60 is merely exemplary and it should be understood that any of one or more of the first valve member 60, the second valve member 62, the first valve member 102, and/or the second valve member 104 may include the slit configuration described with respect to FIG. 7B. For clarity, not all of the features of the first valve member 60 have been identified in FIG. 7B. The central region 76 of the first valve body 72 may include a vertical slit 83 and a horizontal slit 85 extending generally perpendicular to the vertical slit 83. The vertical slit 83 may be formed in the distal side 66 of the first valve member 60 and extend proximally partially through a thickness thereof. In such an instance, the horizontal slit 85 may be formed in the proximal side 64 of the first valve member 60 and extend distally partially through a thickness thereof. The slits 83, 85 may meet in the center of the thickness of the valve member 60 (or at a point between the proximal side 64 and the distal side 66) at their intersection point 87 to define an opening extending entirely through the thickness of the first valve member 60 (e.g., in a cross slit partial (CSP) configuration). The reverse configuration is also contemplated in which the horizontal slit 85 is formed in the distal side 66 of the first valve member 60 and extends proximally partially through a thickness thereof and the vertical slit 83 is formed in the proximal side 64 of the first valve member 60 and extends partially halfway through a thickness thereof.

Figure 7C:
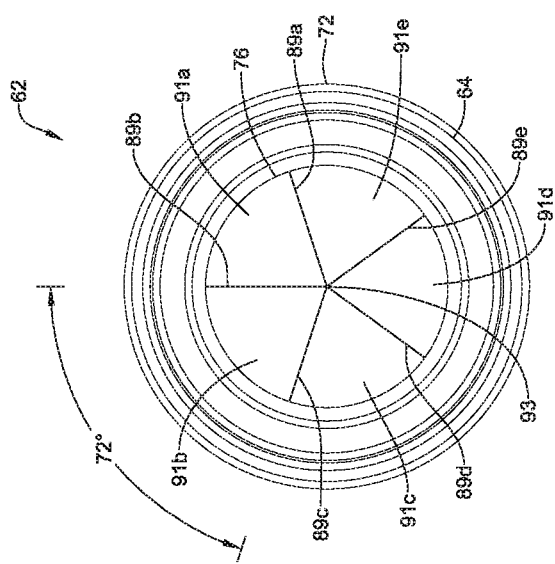
FIG. 7C is a proximal end view of an illustrative valve member having a third slit configuration.

FIG. 7C illustrates a proximal end view of the first valve member 60 having a third slit configuration. The use of the first valve member 60 is merely exemplary and it should be understood that any of one or more of the first valve member 60, the second valve member 62, the first valve member 102, and/or the first valve member 104 may include the slit configuration described with respect to FIG. 7C. For clarity, not all of the features of the first valve member 60 have been identified in FIG. 7C. The central region 76 of the first valve body 72 may include a plurality of slits 89a, 89b, 89c, 89d, 89e (collectively, 89). The slits 89 may be evenly distributed about the central region 76. For example, in the illustrated embodiments, the slits 89 may be spaced approximately 72° from one another. The slits 89 may extend entirely through the thickness of the first valve member 60 from the proximal side 64 to the distal side 66 (e.g., in a star slit thru (SST) configuration). It is contemplated that the slits 89 may also be distributed at irregular intervals (e.g., not evenly spaced), as desired.

The slits 89 may intersect at an intersection point 93 in the diametrical center 65 of the first valve member 60 to define five flaps 91a, 91b, 91c, 91d, 91e (collectively, 91). The number and orientation of slits 89 may be varied to vary a number of flaps 91, as desired. As described herein, the slits 89 may not necessarily intersect at a 72° angle. The intersection angles may be varied to create flaps 91 of varying size. The flaps 91 may bend or flex in the distal direction as the capillary 28 (or other supplemental medical device) is passed through the first valve member 60. Once distal movement of the capillary 28 (or other supplemental medical device) ceased (and the distal biasing force is removed from the first valve member 60), the flow of blood from the distal side 66 may bias the flaps 91 proximally causing the flaps 91 to seal around an outer surface of the capillary 28 (or other supplemental medical device) as well as bringing the flaps 91 into intimate contact adjacent to the slits 89.

Figure 8B:
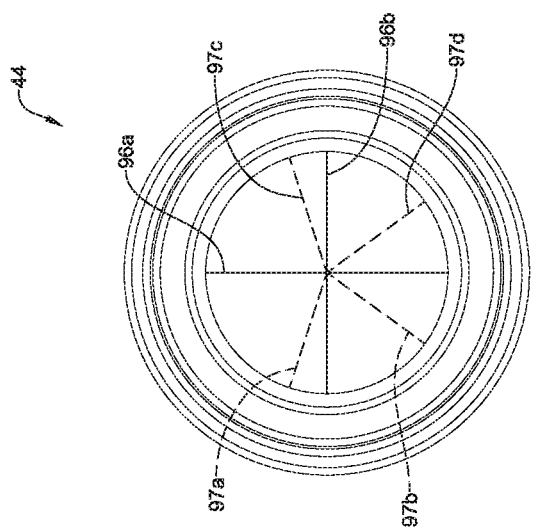
Figure 8C:
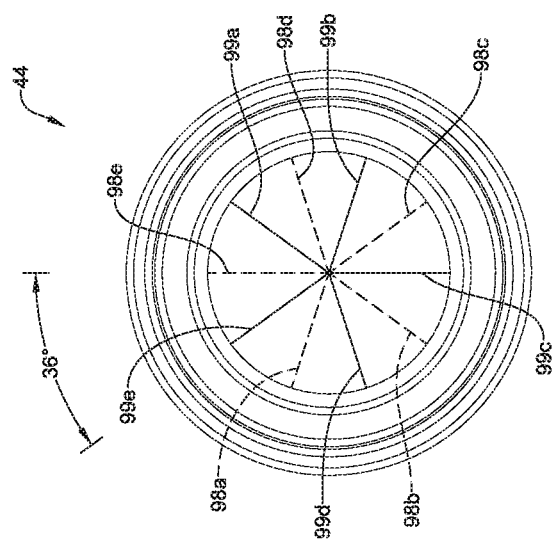

It is contemplated that the slit configuration, orientation, and/or size can be varied to provide maximum protection against leaks. In other words, the first valve member 60 and the second valve member 62 forming the low pressure seal assembly 44 need not have the same slit configuration, orientation, and/or size. Further, the first valve member 102 and the second valve member 104 of the low pressure seal assembly 100 need not have the same slit configuration, orientation, and/or size. FIGS. 8A, 8B, and 8C are proximal end views of the low pressure seal assembly 44 illustrating some possible combinations. However, it should be understood that the first valve member 60 and the second valve member 62 (or the first valve member 102 and the second valve member 104) may be combined in any number of configurations, as desired.

FIG. 8A illustrates an illustrative low pressure seal assembly 44 in which the first valve member 60 and the second valve member 62 each have the CST configuration illustrated in FIG. 7A. However, the slits 94a, 94b of the second valve member 62 are radially offset from the slits 95a, 95b of the first valve member 60 by 45°. Offsetting the slits 94a, 94b, 95a, 95b may improve the leak protection of the low pressure seal assembly 44 by hindering the flow of fluid through the low pressure seal assembly 44 (e.g., removing a direct flow path). FIG. 8B illustrates an illustrative low pressure seal assembly 44 in which the first valve member 60 has the CST configuration illustrated in FIG. 7A and the second valve member 62 has the SST configuration illustrated in FIG. 7C. In such an arrangement, most of the slits 96a, 96b in the first valve member 60 may be radially offset from the slits 97a, 97b, 97c, 97d in the second valve member 62. Offsetting the slits 96a, 96b, 97a, 97b, 97c, 97d may improve the leak protection of the low pressure seal assembly 44 by hindering the flow of fluid through the low pressure seal assembly 44 (e.g., removing a direct flow path). FIG. 8C illustrates an illustrative low pressure seal assembly 44 in which the first valve member 60 and the second valve member 62 each have the SST configuration illustrated in FIG. 7C. However, the slits 98a, 98b, 98c, 98d, 98e (collectively, 98) of the second valve member 62 are radially offset from the slits 99a, 99b, 99c, 99d, 99e (collectively, 99) of the first valve member 60 by 36°. Offsetting the slits 98, 99 may improve the leak protection of the low pressure seal assembly 44 by hindering the flow of fluid through the low pressure seal assembly 44 (e.g., removing a direct flow path).

The materials that can be used for the various components of the medical devices and/or assemblies 10, 44, 100 (and/or other systems disclosed herein) and the various elements thereof disclosed herein may include those commonly associated with medical devices. For simplicity purposes, the following discussion makes reference to the system 10. However, this is not intended to limit the devices and methods described herein, as the discussion may be applied to other elements, members, components, or devices disclosed herein, such as, but not limited to, the hemostasis valve assembly 10, and/or elements or components thereof.

In some embodiments, the system 10, and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of system 10, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device system 10 to achieve the same result.

In some embodiments, a degree of Magnetic Resonance Imaging (MRI) compatibility is imparted into the medical device system 10. For example, system 10, and/or components or portions thereof, may be made of a material that does not substantially distort the image and create substantial artifacts (e.g., gaps in the image). Certain ferromagnetic materials, for example, may not be suitable because they may create artifacts in an MRI image. The system 10, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, an exterior surface of the medical device system 10 (including, for example, an exterior surface of the delivery system) may be sandblasted, bead-blasted, sodium bicarbonate-blasted, electropolished, etc. In these as well as in some other embodiments, a coating, for example a lubricious, a hydrophilic, a protective, or other type of coating may be applied over portions or all of the outer sheath, or in embodiments without an outer sheath over portions of the delivery system, or other portions of the medical device system 10. Hydrophobic coatings such as fluoropolymers provide a dry lubricity which improves device handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A hemostasis valve assembly for use in a medical device, the hemostasis valve assembly comprising:
   a main body portion defining an internal cavity;
   a seal cartridge disposed within the internal cavity; and
   a low pressure valve assembly positioned within the internal cavity adjacent to the seal cartridge, the low pressure valve assembly comprising:
   a first valve member including a first valve body having a proximal side, a distal side, and a thickness therebetween, an entirety of the distal side of the first valve member is planar, the entirety of the distal side extending from an outer edge of the first valve member to a center point of the first valve member, the proximal side of the first valve member has an angled central region sloped towards a diametrical center of the first valve member; and
   a second valve member including a second valve body having a proximal side, a distal side, and a thickness therebetween, the distal side of the second valve member has an angled central region;
   wherein at least a portion of the distal side of the first valve member directly abuts at least a portion of the proximal side of the second valve member;
   wherein both the first and second valve members comprise an elastomeric material.

2. The hemostasis valve assembly of claim 1, wherein the angled central region of the distal side of the second valve member is sloped proximally towards a diametrical center, and the proximal side of the second valve member is generally planar.

3. The hemostasis valve assembly of claim 1, wherein the proximal side of the second valve member is generally planar and wherein the distal side of the second valve member is sloped distally towards a diametrical center.

4. The hemostasis valve assembly of claim 1, wherein both the first and second valve members of the low pressure valve assembly comprise an elastomeric silicone.

5. The hemostasis valve assembly of claim 1, wherein the first valve member comprises a first elastomeric material and the second valve member comprises a second elastomeric material different from the first elastomeric material.

6. The hemostasis valve assembly of claim 1, further comprising:
   one or more slits formed in the first valve body and extending at least partially through the thickness of the first valve body; and
   one or more slits formed in the second valve body and extending at least partially through the thickness of the second valve body.

7. The hemostasis valve assembly of claim 6, wherein the one or more slits in the first valve body and the one or more slits in the second valve body are formed in a cross slit thru (CST) configuration, a star slit thru (SST) configuration, a cross slit partial (CSP) configuration, or combinations thereof.

8. The hemostasis valve assembly of claim 6, wherein the one or more slits in the first valve body are radially offset from the one or more slits in the second valve body.

9. A hemostasis valve assembly for use in a medical device, the hemostasis valve assembly comprising:
   a main body portion defining an internal cavity;
   a seal cartridge disposed within the internal cavity;
   a low pressure valve assembly positioned within the internal cavity adjacent to the seal cartridge, the low pressure valve assembly comprising:
   a first valve member including a first valve body having a proximal side, a distal side, and a thickness therebetween, the proximal side of the first valve member having an angled central region and an entirety of the distal side of the first valve member being planar, the entirety of the distal side extending from an outer edge of the first valve member to a center point of the first valve member; and
   a second valve member including a second valve body having a proximal side, a distal side, and a thickness therebetween, the distal side of the second valve member having an angled central region and the proximal side of the second valve member being generally planar;
   wherein at least a portion of the distal side of the first valve member directly abuts at least a portion of the proximal side of the second valve member;
   wherein both the first and second valve members comprise an elastomeric material.

10. The hemostasis valve assembly of claim 9, wherein both the first and second valve members of the low pressure valve assembly comprise an elastomeric silicone.

11. The hemostasis valve assembly of claim 9, wherein the first valve member comprises a first elastomeric material and the second valve member comprises a second elastomeric material different from the first elastomeric material.

12. The hemostasis valve assembly of claim 9, further comprising:

one or more slits formed in the first valve body and extending at least partially through the thickness of the first valve body; and one or more slits formed in the second valve body and extending at least partially through the thickness of the second valve body.

13. The hemostasis valve assembly of claim 12, wherein the one or more slits in the first valve body and the one or more slits in the second valve body are formed in a cross slit thru (CST) configuration, a star slit thru (SST) configuration, a cross slit partial (CSP) configuration, or combinations thereof.

14. The hemostasis valve assembly of claim 12, wherein the one or more slits in the first valve body are radially offset from the one or more slits in the second valve body.

15. A hemostasis valve assembly for use in a medical device, the hemostasis valve assembly comprising:
a main body portion defining an internal cavity;
a seal cartridge disposed within the internal cavity;
a low pressure valve assembly positioned within the internal cavity adjacent to the seal cartridge, the low pressure valve assembly comprising:
a first valve member including a first valve body having a proximal side, a distal side, and a thickness therebetween, the proximal side of the first valve member having an angled central region and an entirety of the distal side of the first valve member being planar; and
a single piece second valve member including a second valve body having a proximal side, a distal side, and a thickness therebetween, the proximal side of the second valve member defining a conical central region having a surface sloped towards a center of the second valve body and the distal side of the second valve member defining a distally extending convex central region;
wherein at least a portion of the distal side of the first valve member directly abuts at least a portion of the proximal side of the second valve member;
wherein both the first and second valve members comprise an elastomeric material.

16. The hemostasis valve assembly of claim 15, wherein both the first and second valve members of the low pressure valve assembly comprise one or more elastomeric materials.

17. The hemostasis valve assembly of claim 15, further comprising:
one or more slits formed in the first valve body and extending at least partially through the thickness of the first valve body; and
one or more slits formed in the second valve body and extending at least partially through the thickness of the second valve body.

18. The hemostasis valve assembly of claim 17, wherein the one or more slits in the first valve body and the one or more slits in the second valve body are formed in a cross slit thru (CST) configuration, a star slit thru (SST) configuration, cross slit partial (CSP) configuration, or combinations thereof.

19. The hemostasis valve assembly of claim 17, wherein the one or more slits in the first valve body are radially offset from the one or more slits in the second valve body.

* * * * *